United States Patent [19]

Rosenbrook, Jr.

[11] 4,283,529
[45] Aug. 11, 1981

[54] 3-O-DEMETHYL DERIVATIVES OF SANNAMYCIN C AND ANTIBIOTIC AX-127B-1

[75] Inventor: William Rosenbrook, Jr., Libertyville, Ill.

[73] Assignee: Abbott Laboratories, North Chicago, Ill.

[21] Appl. No.: 126,732

[22] Filed: Mar. 3, 1980

[51] Int. Cl.³ .................... A61K 31/71; C07H 15/22
[52] U.S. Cl. ................................ 536/17 R; 424/180; 536/18
[58] Field of Search ..................... 536/17 B, 17 R

[56] References Cited
U.S. PATENT DOCUMENTS

| | | | |
|---|---|---|---|
| 4,124,756 | 11/1978 | Martin et al. | 536/17 B |
| 4,176,178 | 11/1979 | Martin et al. | 536/17 B |
| 4,187,297 | 2/1980 | Martin et al. | 536/17 B |

*Primary Examiner*—Johnnie R. Brown
*Attorney, Agent, or Firm*—Robert L. Niblack; Gildo E. Fato; Joyce R. Niblack

[57] ABSTRACT

3-O-demethylsannamycin C, 3-O-demethyl-antibiotic AX-127B-1 and their 4-N- and 2′-N-acyl and alkyl derivatives are provided. The compounds are broad spectrum antibiotics and anti-bacterial agents.

25 Claims, No Drawings

3-O-DEMETHYL DERIVATIVES OF SANNAMYCIN C AND ANTIBIOTIC AX-127B-1

BACKGROUND OF THE INVENTION

Sannamycin C and antibiotic AX-127B-1 are relatively new aminoglycoside antibiotics. Sannamycin C is a co-fermentation product of sannamycin A and sannamycin B reported by I. Watanabe et al., *J. Antibiotics*, Vol. 32, No. 10, p. 1066(1979). Antibiotic AX-127B-1 is disclosed in commonly assigned, copending U.S. Ser. No. 008,378, filed Feb. 1, 1979.

Chemical modification of the aminoglycoside antibiotics, as with other classes of antibiotics, have been found to improve the activity, either intrinsic or against resistant strains of organisms, or to reduce the toxicity of the parent antibiotics. And, because of the development of aminoglycoside-resistant strains and inactivation of the parent antibiotics by R-mediated factors which can develop, the search continues for new entities which are either superior to known aminoglycosides or which provide an alternative therapy when resistant organisms develop.

In a related family of aminoglycosides, the fortimicins, 3-O-demethylation has been found to improve the intrinsic activity of the antibiotics. See, for example, U.S. Pat. No. 4,124,756.

The present invention provides 3-O-demethyl derivatives of sannamycin C, antibiotic AX-127B-1 and their derivatives.

SUMMARY

The present invention provides 3-O-demethyl derivatives of sannamycin C, antibiotic AX-127B-1 and derivatives thereof. The compounds are broad spectrum antibiotics which are effective against susceptible strains of Gram-negative and Gram-positive organisms.

DETAILED DESCRIPTION OF PREFERRED EMBODIMENTS

The present invention provides 3-O-demethyl derivatives of sannamycin C, antibiotic AX-127B-1 and their derivatives.

Sannamycin C and antibiotic AX-127B-1 are represented by Formulae I and II, respectively:

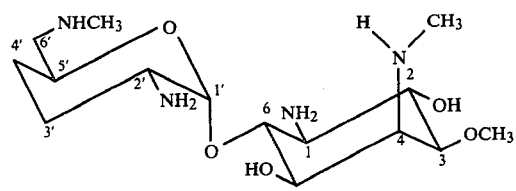

Sannamycin C

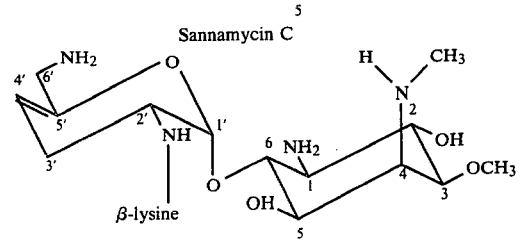

Antibiotic AX-127B-1

The compounds of this invention are represented by Formula III:

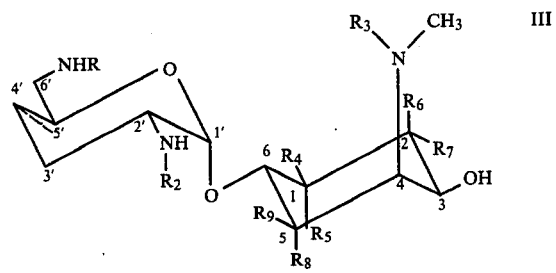

wherein: R is hydrogen or methyl, $R_2$ and $R_3$ are the same or different members of the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl and N,N-diloweralkylaminohydroxyloweralkyl; $R_4$ and $R_5$ are hydrogen or amino with the limitation that one of either $R_4$ or $R_5$ must be hydrogen; $R_6$ and $R_7$ are selected from the group consisting of hydrogen, hydroxy, amino and chloro with the limitation that one of either $R_6$ or $R_7$ must be hydrogen; $R_8$ and $R_9$ or hydrogen or hydroxy with the limitation that one of either $R_8$ or $R_9$ must be hydrogen; and the pharmaceutically acceptable salts thereof.

The term "acyl," as used herein, refers to acyl radicals of loweralkylcarboxylic acids represented by the formula

wherein R is loweralkyl, i.e., acetyl, propionyl, butyryl, valeryl, etc.

The terms, aminoacyl, hydroxy-substituted aminoacyl, etc., enumerated in the definitions for $R_2$ and $R_3$ include, but are not limited to, as will be obvious to one skilled in the art, naturally occuring amino acids such as glycyl, valyl, alanyl, sarcosyl, leucyl, isoleucyl, prolyl, seryl, and like amino acids as well as groups such as 2-hydroxy-4-aminobutyryl, etc. The amino acid residues, with the exception of glycyl, beta-alanyl or other non-assymetric amino acids residues, can be either in the L- or D-configurations or mixtures thereof.

The term "loweralkyl," as used herein, refers to straight or branched chain alkyl radicals containing from 1 to 6 carbon atoms, inclusive, and includes, but is not limited to methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like.

The substituted amino groups are well known in the art and include, for example, beta-aminoethyl, N-methylaminoethyl, N,N-dimethylaminopropyl, hydroxyethyl, 2-hydroxy-4-aminobutyl, and the like.

The term "pharmaceutically acceptable salts" refers to the non-toxic acid addition salts of compounds of this invention which can be prepared either in situ during the final isolation and purification or by separately reacting the free base with a suitable organic or inorganic acid by methods well known in the art. Representative salts include the mono, di, tri, tetra or other per salts such as the hydrochloride, hydrobromide, sulfate, bisulfate, tetrahydrochloride, pentahydrochloride, acetate, oxalate, valerate, oleate, palmitate, stearate, laurate, borate, benzoate, lactate, phosphate, tosylate, citrate, maleate, fumarate, succinate, tartrate, napsylate and like salts and per salts.

The compounds of this invention are useful as antibacterial agents against susceptible or sensitive strains of gram-negative and gram positive bacilli such as *Staphylococcus aureus, Escherichia coli, Pseudomonas aeruginosa Bacillus subtilis, Proteus vulgaris, Shigella sonnei, Salmonella typhi,* and *Klebsiella pneumoniae.*

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

The compounds of this invention are administered parenterally, i.e., intravenously, intramuscularly, intraperitoneally or subcutaneously for systemic effect in daily dosages of from 20 to 80 mg/kg daily, preferably from about 25 to about 60, and most preferably from about 25 to 30 mg/kg of body weight daily, based on lean body weight as is good medical practice with the aminoglycoside antibiotics. It is preferred to administer the compounds of this invention in divided dosages, i.e. three to four times daily. The compounds can also be administered orally at the above dosages to sterilize the intestinal tract and can be further administered in suppository form.

In addition, the compounds can be incorporated into antibacterial solutions and used to sterilize laboratory benchtops, operating room surfaces and the like.

Preparations according to the present invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions and the like. They can also be manufactured in the form of sterile solid compositions which can be dissolved in sterile water or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, i.e. lubricating agents such as magnesium stearate. In the case of capsules, tablets and pills, the dosage forms may also comprise buffering agents. Tablets and pills can additionally be prepared with enteric coatings.

Liquid dosage forms for oral administration also include pharmaceutically acceptable emulsions, solutions, suspensions, syrups and elixirs containing inert diluents commonly used in the art, such as water. Besides the inert diluents, the compositions of this invention can also include adjuvants such as wetting agents, emulsifying agents and suspending agents, as well as sweetening and perfuming agents.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment.

The Sannamycin C derivatives of this invention can be prepared by reacting sannamycin C or the sannamycin C derivative to be O-demethylated with a boron trihalide, preferably boron tribromide, in the presence of an inert solvent such as a halogenated hydrocarbon or hydrocarbon solvent such as methylene chloride which provides solubility for the antibiotic, removal of the solvent and residual boron trihalide, and isolation of the desired product.

Generally speaking, the sannamycin C antibiotic to be O-demethylated is dissolved in, for example, methylene chloride, and the reaction mixture, if necessary to overcome the heat of reaction, is cooled to a temperature of from about $-72°$ C. to about 30° C., preferably about 0° C. and treated with from about 10 to about 100 equivalents of a boron trihalide selected from the group consisting of boron trichloride and boron triiodide, with stirring for about 10 to about 60 minutes at temperatures of between $-72°$ to about 100° C. and preferably from about $-4°$ to about 38° C.

Solvent and residual boron trihalide are then removed in vacuo at a temperature of from about 30° to about 60° C., the reaction mixture treated with an appropriate solvent such as methanol to remove any remaining solvent and boron trihalide and then evaporated to a residue, preferably in vacuo, at a temperature of from about 30° to about 60° C. It is preferred to carry out the latter step twice.

Antibiotic AX-127B-1 can be O-demethylated following treatment with lithium wire in the presence of ethylenediamine. Following completion of the reaction, the mixture of O-demethyl AX 127B-1 and O-demethyl-des-$\beta$-lysyl AX 127B-1 is separated and the desired material recovered. Alternatively, removal of the 2'N-$\beta$-lysyl group with hydrazine, followed by O-demethylation and replacement of the lysyl group affords O-demethyl AX-127B-1, which can then be converted to any desired derivative following standard fortimicin chemistry.

The following examples further illustrate the present invention.

EXAMPLE 1

3-O-Demethylsannamycin C

Twenty-five ml of a two percent solution of sannamycin C free base (500 mg, 1.4 mmole) in methylene chloride (stored over Type A molecular sieve) was cooled to 0° C. and treated with boron tribromide (1.3 ml, 3.5 g, 14 mmole). The mixture was stirred under a drying tube for 30 minutes at 0° C. and then for 16 hours at room temperature. Solvent and residual boron tribromide were removed in vacuo at 40° C. (bath). Methanol (20 ml) was added to the reaction mixture and evaporated to a residue in vacuo at 40° C. (bath) and the last step repeated two times.

3-O-Demethylsannamycin C free base (192 mg) was isolated from the latter residue in a 41 percent yield by silica gel column chromatography using methylene chloride-methanol-concentrated ammonia[4:4:1 (v/v/v)] as a white foam. This can be converted into the desired salt, as can be product of Example 1, by titration with the appropriate acid.

EXAMPLE 2

Fermentation of Antibiotic AX-127-B1

Cultivation of a culture of *Micromonaspora pilosopora* NRRL 11415 may be carried out in a variety of liquid media. Thus, assimilable carbon sources such as glucose, sucrose, fructose, starch, molasses and dextrin either alone or in combination may be used. Organic and inorganic nitrogen sources such as soybean meal or flour, peptone, meat extract, corn steep liquor, amino acids, dried yeast, yeast extract, urea, ammonium sulfate, ammonium chloride, ammonium nitrate and sodium nitrate alone or in combination may be used. Inorganic salts such as potassium chloride, sodium chloride, calcium carbonate and phosphates may also be added to the medium. Other organic or inorganic ingredients may be added to stimulate production of the antibiotic.

A liquid, submerged, stirred culture process is preferred for the production of this antibiotic. Fermentations are carried out at a temperature range of 25° to 37° C. and the pH of the fermentation is preferably maintained between 6 and 9. Antibiotic is produced and accumulated between 3 and 12 days after inoculation of the fermentation.

EXAMPLE 3

Isolation of Antibiotic AX-127-B1

Isolation and purification of antibiotic AX-127B-1 is accomplished by methods ordinarily employed for recovery of water soluble basic antibiotics from fermentation broths. These methods include, but are not restricted to, adsorption on and desorption from cation exchange resins or active carbon, chromatography on the above materials or on silica gel, cellulose, cross-linked dextran, etc., and extraction from water into a water immiscible solvent by ion-pair formation with a strongly acidic, highly lipophilic agent such as lauryl sulfonic acid.

It has been found most convenient to separate the crude antibiotic from the fermentation broth by contacting the broth with a cation exchange resin, such as a co-polymer of acrylic acid and divinyl benzene, or methacrylic acid and divinyl benzene, (such products are sold by the Rohm & Haas Company under the brand name AMBERLITE, specifically AMBERLITE IRC 84, IRC 72, or IRC 50) and, after washing the resin with water, eluting with aqueous ammonia, concentrating the resulting solution under vacuum until the ammonia is gone, and adjusting the pH of the concentrated solution to about 6.5 with aqueous sulfuric or hydrochloric acid. The antibiotic salt thus formed may be obtained as a powder by freeze drying or spray-drying or in the case of the sulfate salt, by adding its concentrated aqueous solution with stirring to a water miscible organic solvent, such as methanol.

The crude product obtained as described may be purified considerably by chromatography on a column packed with a cation exchange resin, using a fine mesh product such as pulverized AMBERLITE IRC 50 or a spherical product of similar composition sold by the Fisher Scientific Company under the tradename REXYN 102, developing with a gradient of increasing concentration of ammonia in water, collecting fractions, locating the antibacterial activity by dipping filter paper discs in the fractions, placing the discs on nutrient agar seeded with a test organism sensitive to the antibiotic, incubating the agar plates until the organism has grown out, observing the zones of inhibition around the paper discs, pooling the active fractions, evaporating to remove ammonia and either neutralizing to form a salt or evaporating the solution to dryness to obtain the free base as a solid.

An alternative purification method consists of adsorbing the crude antibiotic on active carbon from an aqueous solution at pH $8 \pm 0.5$, washing the carbon with water, and eluting the antibiotic with dilute acid, e.g., 0.05 N sulfuric acid.

This process is preferably conducted in a column and fractions of the eluate are tested for antibacterial activity before combining. To obtain the sulfate salt of the purified antibiotic, the excess acid is removed by stirring the solution with an anion exchange resin in the basic cycle until the pH is raised above 4.5. The solution is then separated from the resin and evaporated to dryness, or the concentrated solution may be poured with stirring into a water miscible solvent such as methanol to precipitate the salt of the antibiotic. A suitable anion exchange resin, containing tertiary amine groups on a cross linked acrylic polymer, is AMBERLITE IRA-68, but a great variety of anion exchange resins may be used.

If the free base of the antibiotic is to be isolated, the biologically active acidic eluate from the carbon column is passed through a column of a strong base anion exchange resin (such as a styrene-divinyl benzene co-polymer of a low degree of crosslinkage and bearing quaternary ammonium functional groups) in the hydroxide form. Suitable resins for this application are DOWEX 1-X2 or DOWEX 2-X4 manufactured by the Dow Chemical Company, although a number of other brands are available.

EXAMPLE 4

3-O-Demethyl antibiotic AX-127-B1

Lithium wire (12.5 cm) is added as freshly cut 5 mm pieces to 100 ml of ethylenediamine (distilled from sodium) contained in a 500 ml reaction flask equipped with an overhead mechanical stirrer and under a nitrogen atmosphere. After the appearance of a deep blue color (about 5 minutes), antibiotic AX-127-B1 (5.7 mole), dried in vacuo over phosphorus pentoxide, is introduced and the reaction mixture stirred at ambient temperature until the lithium was depleted (30 minutes) at which time, a second addition of lithium wired (12.5 cm) is introduced and the reaction continued for another 3 hours. After the characteristic blue color disappears, the reaction mixture is carefully quenched with methanol (300 ml). Removal of the methanol and ethylenediamine under high vacuum affords a residue which is passed through a column of silica gel (1.5×45 cm) using chloroform-methanol-concentrated ammonia[1:2:1(v/v/v)] to remove the bulk of the salts. Concentration of the appropriate fraction results in crude product which is purified by column chromatography over silica gel using chloroform-2-propanol-concentrated ammonia[2:4:1(v/v/v)]. Removal of solvent from the appropriate fractions yields the desired product.

EXAMPLE 5

3-O-Demethyl antibiotic AX-127-B1

A. Preparation of 2'-N-des-lysyl AX-127-B1

A total of 4.66 g of the sulfate salt of antibiotic AX-127-B1 sulfate salt (prepared according to U.S. Ser. No. 008,378, filed Feb. 1, 1979) was converted to the free base by treatment with AG 2×8 resin (OH$^-$) form, BioRad Laboratories, to afford 2.71 g of the free base after lyophilization. Raman 389, 390, 391, $\mu_{max}$ 1690 cm$^{-1}$. The later was refluxed gently in 25 ml of hydrazine hydrate for 22 hours. Evaporation of the hydrazine left a residue of 2.755 g of crude product. The crude product was chromatographed on 140 g of silica gel in the lower phase of methanol-methylene chloride-ammonium hydroxide[1:1:1(v/v/v)]. Ten ml fractions were collected and a total of 1.325 g of product obtained.

B. O-Demethyl-2'-N-des-lysyl AX-127-B1

2'-N-des-lysyl-AX-127-B1 is O-demethylated according to the method of Example 1 to afford O-demethyl-2'-N-deslysyl-AX-127-B1.

C. O-Demethyl-AX-127-B1

To a stirring, ice bath cooled solution of O-demethyl-AX-127-B1(1.6 g) in 24 ml of water and 48 ml of methanol is added 3.6 g of N-(benzyloxycarbonyloxy)succinimide. The reaction is stirred at icebath temperature for 4 hours and then at room temperature for 22 hours. The reaction is concentrated under reduced pressure and poured into 400 ml of water to which is added 200 ml of chloroform. The organic layer is separated and washed with water and dried over magnesium sulfate. The chloroform is evaporated and the residue is chromatographed on silica gel prepared and eluted with a solvent system consisting of chloroform-methanol-concentrated ammonium hydroxide[23.4:1.4:0.1(v/v/v)]. Fractions containing pure 1,2',6'-tri-N-benzyloxy-3-O-demethyl AX-127-B1 are collected and evaporated to dryness to give the desired intermediate.

To a stirred solution of the above intermediate (0.25 g) N-benzyloxycarbonyl-beta-lysyl (0.1 g) and 1-hydroxy-benzotriazole (0.1 g) in tetrahydrofuran (3 ml) is added N,N'-dicyclohexylcarbodiimide (0.1 g) in tetrahydrofuran (1.5 ml). An additional 1.5 ml of tetrahydrofuran is used to rinse all the N,N'-dicyclohexylcarbodiimide into the reaction flask. Stirring is continued for 16 hours at room temperature. Insoluble dicyclohexylurea is removed by filtration and the filtrate concentrated to yield a solid. The latter is chromatographed on a column of silica gel using a solvent system consisting of benzene-methanol-95% ethanol-concentrated ammonium hydroxide[23.5:1.4:2.0:0.2(v/v/v/v)]. Fractions containing homogeneous material are taken to dryness. Otherfractions containing a minor second component are rechromatographed on a column of silica gel using a solvent system consisting of benzene-methanol-concentrated ammonium hydroxide[85:15:1(v/v/v)]. Homogeneous fractions are combined with material obtained in the first column to yield tetra-N-benzyloxycarbonyl-3-O-demethyl-beta-lysyl-AX-127-B1.

Hydrogenation of the latter in 25 ml of 0.2 N hydrochloric acid in methanol for 4 hours under 3 atmospheres of hydrogen in the presence of 0.1 g of 5% palladium on carbon, removal of the catalyst by filtration, and concentration of the filtrate to dryness under reduced pressure results in crude product. Excess acid is removed by co-distillation with methanol under reduced pressure to yield 4-N-beta-lysyl-3-O-demethyl-2'-N-des-lysyl AX-127B-1. The latter is passed through an ion exchange column to provide the free base, and allowed to stand in water at 37° C. for 20 days. The water is then evaporated under reduced pressure to leave crude product which is chromatographed on a column (2.2×52 cm) of a cation exchange resin, carboxylic type, e.g. Bio Rad Laboratories Bio-Rex 70, 100-200 mesh (ammonium form) and eluted with 0.1 N ammonium hydroxide. Elutes containing only 2-O-demethyl-AX-127B-1 are collected, evaporated to a small volume under reduced pressure and lypholized to give the desired product.

4-N-acyl derivatives of 3-O-demethylsannamycin C and 3-O-demethyl-AX-127B-1 are readily prepared by reacting the compounds with N-(benzyloxycarbonyloxy)succinimide to afford the 1,2',6'-tri-N-benzyloxycarbonyl intermediate according to the procedure set forth in U.S. Pat. No. 4,091,032. The product formed in the above reaction is isolated by column chromatography and 4-N-acylated by treatment with, for example, an active carboxylic acid ester, i.e., a suitable N-benzyloxycarbonyl-protected amino acid ester prepared by the method of M. Fujino et al., *Chem. Pharm. Bull., Japan,* 22, p. 1857(1974). The per-N-protected intermediates are conveniently reduced to the corresponding 4-N-alkyl derivatives with diborane. After isolation with column chromatography, the benzyloxycarbonyl groups of both the 4-N-acyl and 4-N-alkyl derivatives are conveniently removed by catalytic hydrogenolysis and the products can be conveniently isolated as the free base or as a salt.

The 2'-N-acyl and alkyl derivatives of this invention are then readily prepared by rearrangement of the corresponding 4-N-acyl or alkyl-substituted derivative. In one method, the stable acid addition salts of a suitable, 4-N-substituted derivative of 3-O-demethylsannamycin C or 3-O-demethyl-AX-127B-1 are converted to the free bases, by, for example, use of a suitable anion exchange resin. The corresponding 2'-N-derivatives are then prepared by placing the corresponding free base in water solution which readily rearranges the substituent at the nitrogen attached to the $C_4$ carbon to the nitrogen attached to the $C_{2'}$ carbon. Treatment of the 2'-N-substituted derivatives with a suitable acetylating agent such as N-benzyloxycarbonyloxy)succinimide, benzyloxycarbonyl chloride or O-(benzyoxycarbonyl)-p-nitrophenol in a suitable solvent system provides the per-N-protected intermediate which can then be acylated to provide the desired 2'-N-acyl substituent or reduced to provide the desired 2'-N-alkyl substituent.

EXAMPLE 6

3-O-Demethyl-4-N-glycylsannamycin C

3-O-Demethyl-4-N-glycylsannamycin C is prepared according to the method of Example 5, using 3-O-demethylsannamycin C and N-benzyloxycarbonylglycine.

EXAMPLE 7

3-O-Demethyl-4-N-beta-alanylsannamycin C

3-O-Demethyl-4-N-beta-alanylsannamycin C is prepared according to the method of Example 5, using 3-O-demethylsannamycin C and N-benzyloxycarbonyl-beta-alanine.

EXAMPLE 8

3-O-Demethyl-2'-N-glycylsannamycin C

3-O-Demethyl-2'-N-glycylsannamycin C is prepared by placing the compound of Example 6 in a water solution at 37° C. for 20 hours according to the method of Example 5.

EXAMPLE 9

3-O-Demethyl-2'-N-beta-alanylsannamycin C

3-O-Demethyl-2'-N-beta-alanylsannamycin C is prepared by placing the compound of Example 7 in water at 37° C. for 20 hours according to the method of Example 5 and recovering the desired product therefrom.

EXAMPLE 10

3-O-Demethyl-4-N-glycyl-AX-127B-1

3-O-Demethyl-4-N-glycyl-AX-127B-1 is prepared according to the method of Example 5, using N-benzyloxycarbonylglycine in place of N-benzyloxycarbonyl-beta-lysine.

EXAMPLE 11

3-O-Demethyl-2'-N-glycyl-AX-127B-1

3-O-Demethyl-2'-N-glycyl-AX-127B-1 is prepared by placing the compound of Example 10 is water for 20 hours at room temperature according to the method of Example 5, and recovering the desired product therefrom.

EXAMPLE 12

3-O-Demethyl-4-N-(beta-aminoethyl)-AX-127B-1

3-O-Demethyl-4-N-(beta-aminoethyl)-AX-127B is prepared by reacting an ice cold solution of the compound of Example 10 with a 1 M solution of diborane in tetrahydrofuran, with stirring under a nitrogen atmosphere for about 3 hours. Treatment with an additional 1 ml of diborane solution with stirring under a nitrogen atmosphere, addition of water, and evaporation of solvents under reduced pressure yields the crude product. Subsequent purification by column chromatography on silica gel prepared and eluted with a solvent system consisting of chloroform-methanol-concentrated ammonium hydroxide[23.4:4.1:4:0.1(v/v/v/v)] gives the pure product.

EXAMPLE 13

3-O-Demethyl-2'-N-(beta-aminoethyl)-AX-127B-1

3-O-Demethyl-2'-N-(beta-aminoethyl)-AX-127B-1 is prepared according to the method of Example 12 from the compound of Example 11.

I claim:

1. A 3-O-demethylsannamycin C or antibiotic AX-127B-1 derivative represented by the formula

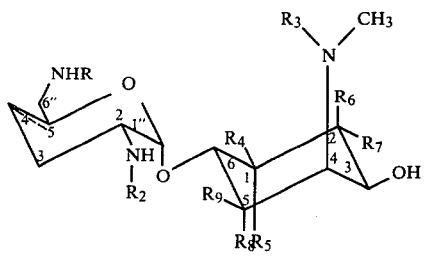

wherein: R is hydrogen or methyl, $R_2$ and $R_3$ are the same or different members of the group consisting of hydrogen, acyl of the formula $$\overset{O}{\underset{\|}{C}}R_{10}$$

wherein $R_{10}$ is loweralkyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl and N,N-diloweralkylaminohydroxyloweralkyl; $R_4$ and $R_5$ are hydrogen or amino with the limitation that one of either $R_4$ or $R_5$ must be hydrogen; $R_6$ and $R_7$ are selected from the group consisting of hydrogen, hydroxy, amino and chloro with the limitation that one of either $R_6$ or $R_7$ must be hydrogen; $R_8$ and $R_9$ are hydrogen or hydroxy with the limitation that one of either $R_8$ or $R_9$ must be hydrogen; and the pharmaceutically acceptable salts thereof.

2. A compound of claim 1 wherein the 4'-5' position is saturated.

3. A compound of claim 2 wherein R is hydrogen.

4. A compound of claim 3 wherein $R_4$ is amino and $R_5$ is hydrogen.

5. A compound of claim 3 wherein $R_4$ is hydrogen and $R_5$ is amino.

6. A compound of claim 3, 4, or 5 wherein $R_9$ is hydroxy and $R_8$ is hydrogen.

7. A compound of claim 3, 4, or 5 wherein $R_9$ is hydrogen and $R_8$ is hydroxy.

8. A compound of claim 3, or 4 wherein $R_6$ is hydrogen and $R_7$ is hydroxy.

9. A compound of claim 3 or 4 wherein $R_7$ is hydrogen and $R_6$ is hydroxy.

10. A compound of claim 2 wherein $R_3$ is hydrogen.

11. A compound of claim 2: 3-O-demethylsannamycin C or a pharmaceutically acceptable salt thereof.

12. A compound of claim 1 wherein the 4'-5'-position is unsaturated.

13. A compound of claim 12 wherein R is hydrogen.

14. A compound of claim 12 wherein R and $R_3$ both are hydrogen.

15. A compound of claim 12 wherein R and $R_3$ each are hydrogen and $R_2$ is beta-lysyl.

16. A compound of claim 15 wherein $R_4$ is amino and $R_5$ is hydrogen.

17. A compound of claim 15 wherein $R_4$ is hydrogen and $R_5$ is amino.

18. A compound of claim 15 wherein $R_6$ is hydrogen and $R_7$ is hydroxy.

19. A compound of claim 15 wherein $R_6$ is hydroxy and $R_7$ is hydrogen.

20. A compound of claim 15 wherein $R_8$ is hydrogen and $R_9$ is hydroxy.

21. A compound of claim 15 wherein $R_8$ is hydroxy and $R_9$ is hydrogen.

22. 3-O-Demethylsannamycin C or a pharmaceutically acceptable salt thereof.

23. 3-O-Demethyl-antibiotic AX-127B-1 or a pharmaceutically acceptable salt thereof.

24. 3-O-Demethyl-2'-N-deslysyl-antibiotic AX-127B-1 or a pharmaceutically acceptable salt thereof.

25. 3-O-Demethyl-2'-N-des-lysyl-4-N-beta-lysyl-antibiotic-AX-127B-1 or a pharmaceutically acceptable salt thereof.

* * * * *